US00PP24135P2

(12) United States Plant Patent
NeSmith

(10) Patent No.: US PP24,135 P2
(45) Date of Patent: Jan. 7, 2014

(54) RABBITEYE BLUEBERRY PLANT NAMED 'T-959'

(50) Latin Name: *Vaccinium ashei*
Varietal Denomination: T-959

(75) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 55 days.

(21) Appl. No.: 13/134,495

(22) Filed: Jun. 8, 2011

(51) Int. Cl.
*A01H 5/00* (2006.01)

(52) U.S. Cl.
USPC ..... Plt./157

(58) Field of Classification Search
USPC ..... Plt./157
See application file for complete search history.

*Primary Examiner* — Kent L Bell
(74) *Attorney, Agent, or Firm* — Klarquist Sparkman, LLP

(57) ABSTRACT

The variety 'T-959' ripens around the first week of June in southern Georgia. The fruits of the new 'T-959' variety are very large, firm, and have good flavor. The new 'T-959' variety is vigorous with an estimated chilling requirement of about 500 to 550 hours at or below approximately 7° C. The new variety is reliably propagated vegetatively.

3 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'T-959' is a *Vaccinium ashei* rabbiteye blueberry plant.

Variety denomination: The new rabbiteye blueberry plant claimed is a new variety denominated 'T-959'.

BACKGROUND OF THE INVENTION

The present invention relates to the discovery of a new and distinct cultivar of rabbiteye blueberry plant, herein referred to as 'T-959', as herein described and illustrated.

The new blueberry plant variety 'T-959' was selected in Griffin, Ga. in 2005. The new variety 'T-959' ripens around the first week of June in southern Georgia. The fruit of the new variety 'T-959' are large and have good flavor. The new variety 'T-959' is vigorous with an estimated chilling requirement of about 500-550 hours at or below approximately 7° C.

Pedigree and history: 'T-959' was selected in 2005 in Griffin, Ga., originating from a cross of 'T-460'×'FL 80-11' made by Dr. Scott NeSmith in 2002. The two parents are non-patented blueberry breeder selections that have not been produced commercially. The selection has been tested in plantings at Alapaha and Griffin, Ga. established in the Fall of 2006.

The new blueberry plant variety 'T-959' has been shown to maintain its distinguishing characteristics through successive asexual propagations by softwood cuttings in Alapaha and Griffith, Ga. Plants from softwood cuttings have been directly planted in the ground.

SUMMARY OF THE INVENTION

The new blueberry plant variety 'T-959' has not been observed under all possible environmental conditions. The phenotype may vary somewhat with variations in environment and cultural practices such as temperature and light intensity without, however, any variance in genotype.

The following traits of the new 'T-959' variety have been repeatedly observed in Alapaha and Griffin Ga., and have been determined to be the unique combination characteristics of the new rabbiteye blueberry plant variety 'T-959':

1. Very large berry size;
2. Excellent plant vigor;
3. Excellent fruit firmness.

The new variety 'T-959' can be compared to the rabbiteye blueberry varieties 'Alapaha' (the subject of U.S. Plant Pat. No. 16,266), 'Vernon' (the subject of U.S. Plant Pat. No. 18,291), 'Premier', and 'Brightwell' (both non-patented commercial blueberry varieties).

Comparison: The 'T-959' variety has berries that ripen around the time of the early rabbiteye varieties 'Alapaha', 'Vernon' and 'Premier', but before the mid-season variety 'Brightwell'. 'T-959' has very large, firm berries, and the plant has a high degree of plant vigor as compared over a three year time period to the other varieties grown in Griffin and Alapaha, Ga. (Tables 1 and 2). Table 3 depicts berry weight for 'T-959' and comparison cultivars from both Griffin and Alapaha locations for the first 25% of ripe fruit. In each of the sets from the site/years, 'T-959' has had much greater average berry weight than all of the other compared cultivars. 'Alapaha' was released in 2001, as a new early season variety with consistent cropping, and was followed by 'Vernon' in 2004 for an early season companion variety with larger berry size to compete with the much older standard 'Premier'. 'T-959' is superior to each of these with respect to berry size. 'T-959' has much larger berries than the popular early-mid season older variety 'Brightwell'. While yield data is limited, Table 4 depicts total yield per plant taken from three single plant replicates via hand harvesting in selection test plots at Alapaha in 2009 and 2010, and in Griffin in 2010. These data support that 'T-959' is a high yielding plant, primarily due to the large berry size. The total yield of 23.1 lbs per plant for 'T-959' from Alapaha in 2010 is the largest yield that the inventor has ever recorded for 4 year old plants. In addition to large berry size, 'T-959' berries also demonstrate excellent firmness (Table 5). 'Brightwell' is considered the standard for firmness in the industry, which makes it useful for machine harvesting and long distant shipping. 'T-959' had equal or greater firmness than 'Brightwell' (as measured with a specialized laboratory instrument called a FirmTech 2) in each of 3 years in Griffin. The 'T-959' variety also had greater firmness than 'Alapaha', 'Vernon', and 'Premier'.

In comparison to its 'T-460' parent, 'T-959' has much larger berries ('T-460' avg 1.8 to 2.4 g vs 3.0 to 4.0 g for 'T-959'), 'T-959' has greater plant vigor, and 'T-959' ripens 6 to 9 days earlier than 'T-460'.

In comparison to its 'FL 80-11' parent, 'T-959' has much larger berries ('FL-80-11' avg is 2.0 to 2.5 g vs 3.0 to 4.0 g for 'T-959'), and 'T-959' flowers some 5 to 8 days later than 'FL-80-11', while ripening at a similar time.

TABLE 1

Average ratings of some fruit and plant characteristics of 'T-959' and rabbiteye standard cultivars 'Alapaha', 'Vernon', 'Premier', and 'Brightwell' from 2008-2010 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in Fall 2006.

| Berry and plant attributes[y] | Cultivar | | | | |
|---|---|---|---|---|---|
| | 'T-959' | 'Alaphaha' | 'Vernon' | 'Premier' | 'Brightwell' |
| Berry size | 9.5 ± 0.2 | 6.9 ± 0.1 | 7.9 ± 0.2 | 7.8 ± 0.2 | 7.0 ± 0.1 |
| Berry scar | 8.2 ± 0.2 | 7.6 1 0.1 | 8.0 ± 0.1 | 7.7 ± 0.2 | 7.7 ± 0.2 |
| Berry color | 7.3 ± 0.1 | 7.0 ± 0.1 | 7.2 ± 0.2 | 7.5 ± 0.3 | 7.3 ± 0.2 |
| Berry firmness | 8.3 ± 0.3 | 7.0 ± 0.2 | 7.7 ± 0.3 | 6.9 ± 0.2 | 7.7 ± 0.2 |
| Berry flavor | 7.0 ± 0.1 | 7.8 ± 0.1 | 7.7 ± 0.2 | 7.8 ± 0.1 | 7.0 ± 0.2 |
| Cropping | 6.3 ± 0.5 | 6.2 ± 0.2 | 4.5 ± 1.0 | 2.5 ± 0.3 | 7.8 ± 1.0 |
| Plant vigor | 10.0 ± 0.1 | 8.0 ± 0.1 | 8.8 ± 0.1 | 9.3 ± 0.4 | 9.2 ± 0.6 |
| Date of 50% flowering | March 21 | March 22 | March 20 | March 23 | March 25 |
| Date of 50% ripening | June 1 | June 4 | June 2 | June 6 | June 19 |
| Fruit development period (days) | 73 ± 3.2 | 75 ± 2.0 | 74 ± 4.5 | 75 ± 3.5 | 86 ± 4.5 |

[y]Values are means ± the standard error with n = 3.

TABLE 2

Average ratings of some fruit and plant characteristics of 'T-959' and rabbiteye standard cultivars 'Alapaha', 'Vernon', 'Premier', and 'Brightwell' from 2008-2010 in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in the Fall of 2006.

| Berry and plant attributes[y] | Cultivar | | | | |
|---|---|---|---|---|---|
| | 'T-959' | 'Alapaha' | 'Vernon' | 'Premier' | 'Brightwell' |
| Berry size | 9.6 ± 0.2 | 7.1 ± 0.2 | 8.0 ± 0.3 | 7.7 ± 0.2 | 6.8 ± 0.2 |
| Berry scar | 8.2 ± 0.2 | 7.7 ± 0.3 | 7.8 ± 0.2 | 7.5 ± 0.3 | 7.7 ± 0.2 |
| Berry color | 7.3 ± 0.1 | 7.0 ± 0.1 | 7.2 ± 0.2 | 7.3 ± 0.4 | 7.4 ± 0.2 |
| Berry firmness | 8.3 ± 0.3 | 7.2 ± 0.2 | 7.8 ± 0.2 | 6.8 ± 0.1 | 8.1 ± 0.1 |
| Berry flavor | 7.2 ± 0.2 | 7.9 ± 0.1 | 8.0 ± 0.1 | 7.7 1 0.2 | 7.1 ± 0.2 |
| Cropping | 5.5 ± 0.6 | 5.2 ± 1.3 | 4.2 ± 0.9 | 3.2 ± 0.7 | 6.0 ± 2.1 |
| Plant vigor | 9.8 ± 0.1 | 8.3 ± 0.2 | 8.2 ± 0.4 | 7.8 ± 0.3 | 8.3 ± 0.2 |
| Date of 50% flowering | April 6 | April 3 | April 2 | April 2 | April 5 |
| Date of 50% ripening | June 20 | June 16 | June 14 | June 16 | June 28 |
| Fruit development period (days) | 75 ± 2.0 | 74 ± 2.5 | 73 ± 3.5 | 75 ± 2.0 | 86 ± 2.3 |

[y]Values are means ± the standard error with n = 3.

TABLE 3

Average berry weight for 'T-959' and four standard rabbiteye blueberry cultivars at Griffin and Alapaha research farm locations during 2008 thru 2010. Average berry weights were determined from multiple berry samples (25 to 50 fruit per sample) taken from the first 25% of ripe fruit.

| Variety | 2008 | | 2009 | | 2010 | |
|---|---|---|---|---|---|---|
| | Griffin Location | Alapaha Location | Griffin Location | Alapaha Location | Griffin Location | Alapaha Location |
| | Average berry wt (g)[y] | | | | | |
| 'T-959' | 4.0 ± 0.1 | 4.4 ± 0.2 | 4.2 ± 0.1 | 3.3 ± 0.1 | 3.1 ± 0.2 | 3.2 ± 0.1 |
| 'Alapaha' | 1.6 ± 0.1 | — | 1.8 ± 0.1 | 1.4 ± 0.1 | 1.8 ± 0.1 | 1.4 ± 0.1 |
| 'Vernon' | 2.0 ± 0.1 | — | 2.3 ± 0.1 | 2.1 ± 0.1 | 2.2 ± 0.1 | 2.1 ± 0.1 |
| 'Premier' | 1.8 ± 0.1 | 1.6 ± 0.1 | 2.1 ± 0.1 | 1.8 ± 0.1 | 2.0 ± 0.1 | 1.7 ± 0.1 |
| 'Brightwell' | 1.5 ± 0.1 | — | 1.6 ± 0.1 | 1.5 ± 0.1 | 1.2 ± 0.1 | 1.6 ± 0.1 |

[y]Values are means ± the standard error with n = 3.

TABLE 4

Total yield (lbs/plant) for 'T-959' and three standard rabbiteye blueberry cultivars at Griffin (2010) and Alapaha (2009 and 2010) research farm locations during 2009 and 2010. Total yields were obtained from 3 to 5 hand-harvests at each location from plants established in the Fall of 2006. Three single plant replicates were harvested for each variety at each location.

| Variety | 2009 | | 2010 | |
|---|---|---|---|---|
| | Griffin Location | Alapaha Location | Griffin Location | Alapaha Location |
| | Total yield per plant (lbs)[y] | | | |
| 'T-959' | — | 12.3 ± 0.4 | 14.7 ± 2.6 | 23.1 ± 1.1 |
| 'Alapaha' | — | 7.7 ± 1.1 | 10.8 ± 0.4 | 17.4 ± 1.2 |
| 'Vernon' | — | 5.3 ± 0.9 | 10.8 ± 0.9 | 10.3 ± 0.2 |
| 'Brightwell' | — | 8.6 ± 1.5 | 4.2 ± 0.7 | 15.6 ± 1.5 |

[y]Values are means ± the standard error with n = 3.

TABLE 5

Average berry firmness for 'T-959' and four standard rabbiteye blueberry cultivars at the Griffin research farm location during 2008 thru 2010. Average berry firmness was determined from multiple 25-berry samples using a FirmTech 2 firmness device. Fruit samples were taken from the first 25% of ripe fruit.

| Variety | 2008 | 2009 | 2010 |
|---|---|---|---|
| | Average berry firmness (g/mm)[y] | | |
| 'T-959' | 237 ± 8.3 | 213 ± 2.0 | 260 ± 18.5 |
| 'Alapaha' | 221 ± 3.1 | 194 ± 2.1 | 210 ± 9.1 |
| 'Vernon' | 208 ± 4.7 | 191 ± 1.9 | 206 ± 15.6 |
| 'Premier' | 199 ± 5.9 | 172 ± 3.5 | 165 ± 3.8 |
| 'Brightwell' | 211 ± 10.5 | 216 ± 1.0 | 241 ± 8.9 |

[y]Values are means ± the standard error with n = 4.

BRIEF DESCRIPTION OF THE FIGURES

The accompanying photographic illustrations show typical specimens in full color of the foliage and fruit of the new variety 'T-959'. The colors are as nearly true as is reasonably possible in a color representation of this type. The colors of illustrations of this type may vary with lighting and other conditions. Therefore, color characteristics of this new variety should be determined with reference to the observations described herein, rather than from these illustrations alone.

BOTANICAL DESCRIPTION

Figure 1:
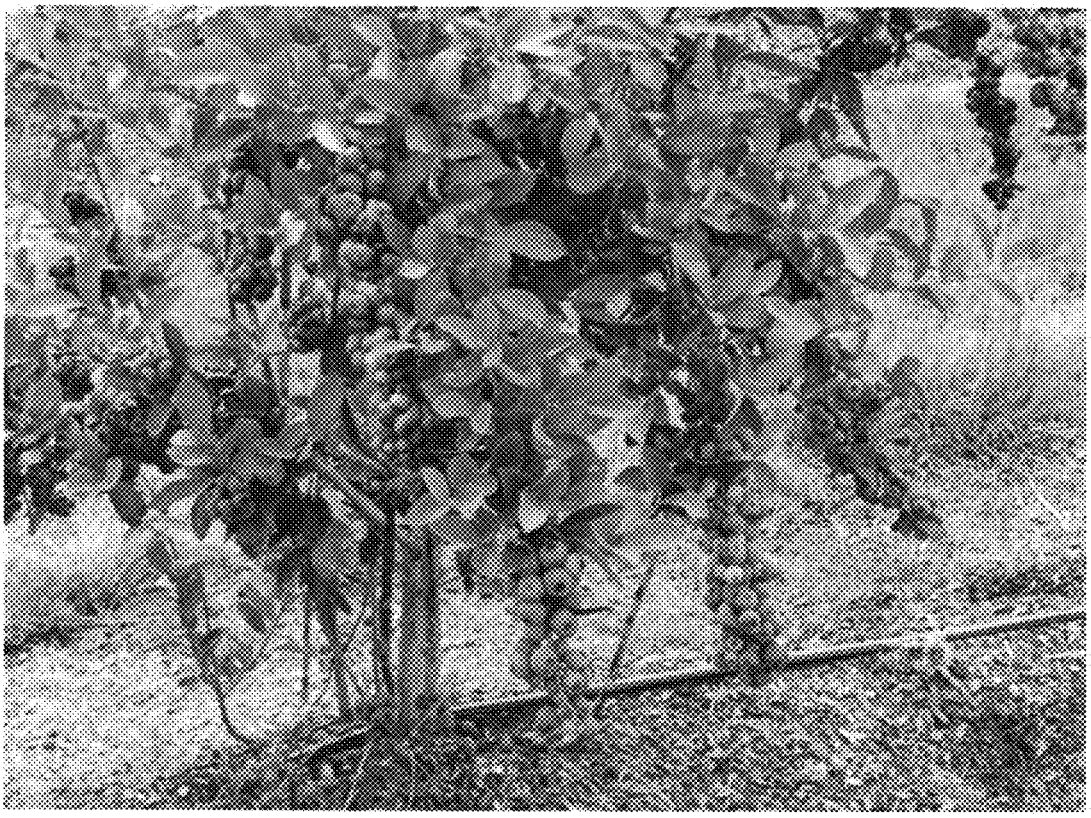
FIG. 1 is a close-up photograph of a typical 3-year old plant of the new variety 'T-959'.
Figure 2:
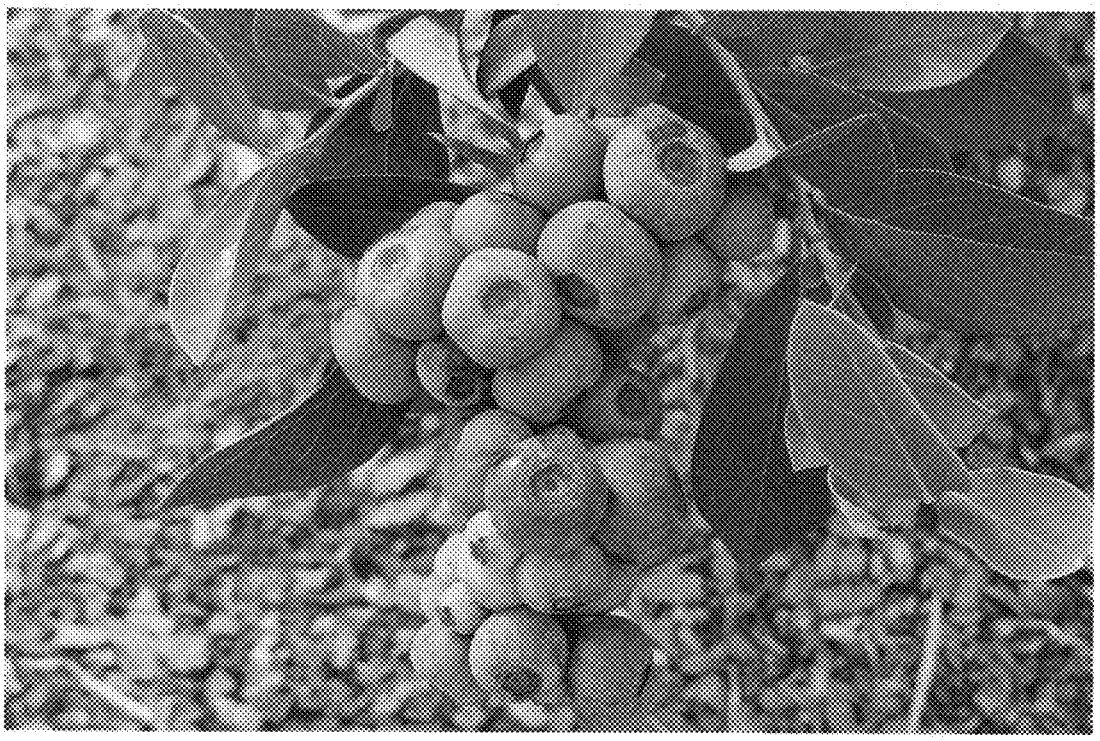
FIG. 2 is a photograph of the fruit of the new variety 'T-959' during ripening.
Figure 3:
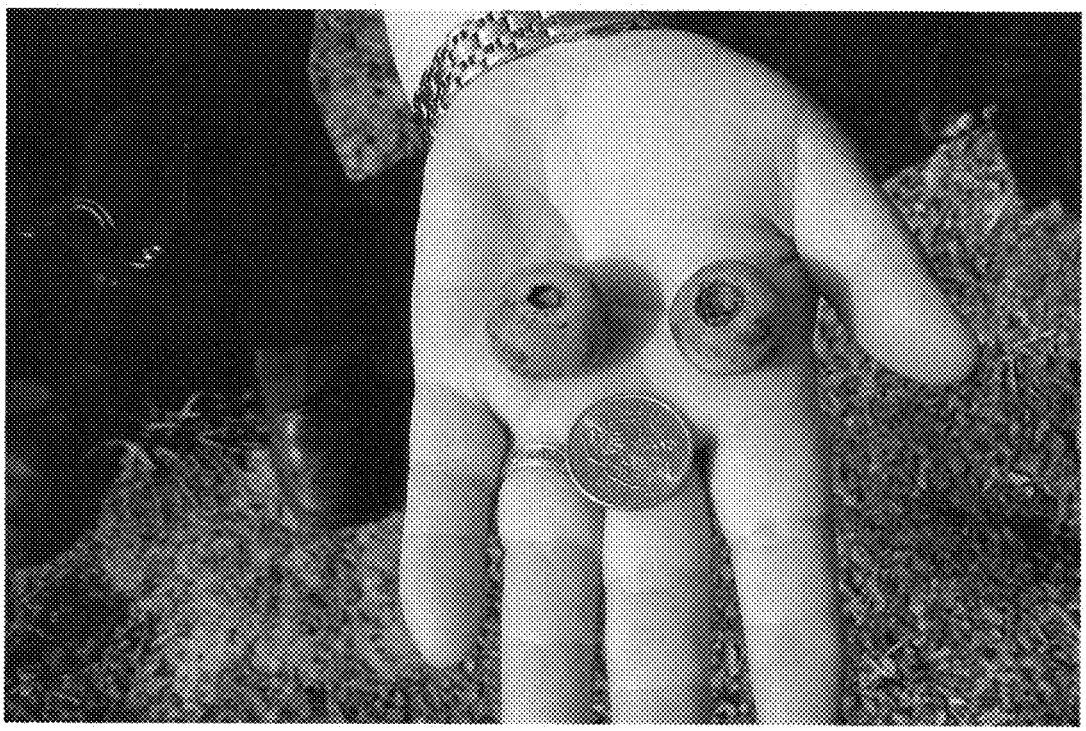
FIG. 3 is a photograph of typical fruit of the new variety 'T-959' as compared to a U.S. quarter coin.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical and pomological characteristics of the new variety 'T-959'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 4 to about 5 years old.

PLANT

Size: 1.5 to 1.8 m tall and 1.2 to 1.5 m in diameter in the upper portion of the plant canopy and 0.3 to 0.4 m diameter at the base or crown by about 4 years of age.

Growth habit: Semi-upright to upright with 2 to 4 canes arising from the crown.

Growth: Highly vigorous.

Productivity: High to very high yield, averaging 15 to 23 lbs of fruit per plant each year for 4 to 5 year old plants grown in soil amended with pine bark and having supplemental irrigation.

Hardiness: Similar to the rabbiteye cultivars 'Alapaha' and 'Vernon'.

Chilling requirement: 500 to 550 hours of temperatures at or below about 7° C. (about 45° F.) to induce normal leafing and flowering during the spring.

Leafing: Plants readily break numerous leaf buds simultaneously with anthesis.

Canes:

*Diameter.*—25 to 40 mm in plants that are about 4 years old and older. 8 to 12 mm in about 2 year old wood. 3 to 5 mm in current season wood.

*Color.*—Grey RHS 201C in plants that are about 4 years old and older. Yellow-green RHS 146C in about 2 year old wood. Yellow-green RHS 145C in current season wood.

*Texture.*—Current season wood: smooth surface 2 year old wood: smooth transitioning to semi-rough.

*Internode length.*—On current season wood is 20 to 35 mm.

FOLIAGE

Leaf color: Healthy mature leaves.

*Top side.*—Green RHS N138B and glaucous.

*Under side.*—Green RHS 148C.

Leaf arrangement: Alternate, simple.

Leaf shape: Elliptic.

Leaf margins: Entire with occasional slight undulations.

Leaf venation: Reticulate.

Leaf apices: Broadly acute.

Leaf bases: Acute.

Leaf dimensions:

*Length.*—65 to 75 mm.

*Width.*—30 to 35 mm.

Petioles: Small.

*Length.*—3.0 to 4.0 mm.

*Width.*—1.8 to 2.0 mm.

*Color.*—Yellow-green RHS 145B with some reddening (Greyed-red 180C) on many petioles.

FLOWERS

Date of 50% anthesis: March 21 (3 year average) in southeast Georgia; April 6 (3 year average) in middle Georgia.

Flower shape: Urceolate.

Flower bud number: High.

Flowers per cluster: 7 to 10.

Flower arrangement: individual flowers arranged alternately along peduncle.

Flower fragrance: None.

Corolla

*Color.*—White RHS N155C (open flower).

*Texture.*—Smooth.

*Length.*—7.5 to 8.5 mm.

*Depth.*—About 7.5 to 8.5 mm.

*Width.*—6.0 to 7.0 mm.

*Aperture width.*—2.0 to 3.0 mm.

Flower peduncle:

*Length.*—10 to 12 mm.

*Color.*—Green RHS 139D.

*Texture.*—Smooth.

Flower pedicel:

*Length.*—4.5 to 5.0 mm.

*Color.*—Yellow-green RHS 146C.

*Texture.*—Smooth.

Calyx (with sepals):

*Diameter.*—5.5 to 6.0 mm.

*Color (sepals).*—Upper surface: Green RHS 137B.

Sepals:

*General.*—Most pronounced at flowering time, becomes much less pronounced at fruit maturity.

*Number.*—Five sepals.

*Size and shape.*—Rounded apex and base; sepal length 1.5 mm to 2.0 mm; sepal width 1.5 mm to 2.0 mm just after corolla drop.

*Sepal margins and surfaces.*—Typically smooth.

Stamen:

*Length.*—6.0 to 6.5 mm.

*Number per flower.*—10.

*Filament color.*—Yellow-green RHS 145D.

Style:

*Length.*—9.5 to 10.5 mm.

*Color.*—Yellow-green RHS 146C.

Pistil:

*Length.*—11.0 to 13.0 mm.

*Ovary color (exterior).*—Green RHS 138B.

Anther:

*Length.*—3.0 to 3.5 mm.

*Number.*—10.

*Color.*—Greyed-Orange RHS 165B.

Pollen:

*Abundance.*—Low to medium.

*Color.*—Yellow-orange RHS 18C.

Self-compatibility: The cultivar has demonstrated a low degree of self-compatibility.

FRUIT

Date of 50% maturity: June 1 (3 year average) in southeast Georgia; June 20 (3 year average) in middle Georgia. Avg first harvest date in southeast Georgia is May 25 and middle Georgia is June 12. Avg last date of harvest in southeast Georgia is June 10 and in middle Georgia is June 30.

Fruit development period: 73 to 77 days.

Berry cluster density: Typical number of berries per cluster: greatly depends on pollination and fruit set, but can avg 4 to 7 berries per cluster.

Berry color:

*With wax.*—Violet-blue RHS 97B.

*With wax removed.*—Black RHS 203B.

Berry surface wax abundance: Medium.

Berry flesh color: White RHS 155C.

Berry weight:

*First harvest.*—3.0 g to 4.0 g.

*Second harvest.*—2.7 g to 3.2 g.

Berry size:

*Height from calyx to scar.*—15.0 to 18.0 mm.

*Diameter.*—17.0 to 23.0 mm.

Berry shape: Semi-spherical, slightly disk shaped.

Fruit stem scar: Small to medium, dry, no tearing at harvest.

Berry firmness: Excellent.

Berry flavor and texture: Good sweet flavor; firm skin and berry flesh.

Storage quality: Excellent.

Suitability for mechanical harvesting: Likely very suited.

Uses: Primarily can be used as fresh fruit for shipping, but also can be used for customer-pick and for processing markets.

SEED

Seed abundance in fruit: Medium to high.

Seed color: Greyed-orange RHS 164A.

Seed dry weight: 54.8 mg per 100 seeds.

Seed size: 1.2 to 2.0 mm long for fully developed seeds; diameter: 0.2 to 0.3 mm.

DISEASE/PEST RESISTANCE/SUSCEPTABILITY

Disease resistance/susceptibility: Similar to rabbiteye varieties 'Premier' and 'Climax'. No notable resistances or susceptibilities.

Pest resistance/susceptibility: Gall midge susceptible. Susceptible to fruit cracking under wet conditions.

What is claimed is:

1. A new and distinct variety of rabbiteye blueberry plant named 'T-959', substantially as illustrated and described herein.

* * * * *